(12) United States Patent
Snyder et al.

(10) Patent No.: US 8,404,269 B2
(45) Date of Patent: Mar. 26, 2013

(54) SUSTAINED RELEASE IMPLANTABLE EYE DEVICE

(76) Inventors: Michael Snyder, Montgomery, OH (US); Eric M. Dobrusin, Bloomfield Hills, MI (US)

(*) Notice: Subject to any disclaimer, the term of this patent is extended or adjusted under 35 U.S.C. 154(b) by 2895 days.

(21) Appl. No.: 10/821,745

(22) Filed: Apr. 9, 2004

(65) Prior Publication Data

US 2005/0008673 A1 Jan. 13, 2005

Related U.S. Application Data

(60) Provisional application No. 60/462,284, filed on Apr. 11, 2003.

(51) Int. Cl.
*A61F 2/00* (2006.01)
*A61F 13/00* (2006.01)
*A61B 18/18* (2006.01)

(52) U.S. Cl. ............. 424/427; 424/422; 424/423; 606/6

(58) Field of Classification Search .......................... None
See application file for complete search history.

(56) References Cited

U.S. PATENT DOCUMENTS

| | | | |
|---|---|---|---|
| 4,743,255 A * | 5/1988 | Bardenstein | 623/6.56 |
| 4,853,224 A | 8/1989 | Wong | |
| 5,273,751 A | 12/1993 | Dubroff | |
| 5,278,202 A * | 1/1994 | Dunn et al. | 523/113 |
| 5,282,829 A * | 2/1994 | Hermes | 606/219 |
| 5,375,611 A | 12/1994 | Lindqvist et al. | |
| 5,401,880 A | 3/1995 | Clark et al. | |
| 5,512,055 A * | 4/1996 | Domb et al. | 604/265 |
| 5,554,187 A | 9/1996 | Rizzo, III | |
| 5,569,463 A | 10/1996 | Helmus et al. | |
| 5,616,122 A | 4/1997 | Lam et al. | |
| 5,624,704 A | 4/1997 | Darouiche et al. | |
| 5,743,274 A | 4/1998 | Peyman | |
| 5,820,917 A | 10/1998 | Tuch | |
| 5,843,184 A | 12/1998 | Cionni | |
| 5,843,186 A | 12/1998 | Christ | |
| 5,853,760 A | 12/1998 | Cremer | |
| 5,876,438 A | 3/1999 | Kelleher et al. | |
| 5,902,283 A | 5/1999 | Darouiche et al. | |
| 5,980,928 A | 11/1999 | Terry | |
| 6,074,661 A * | 6/2000 | Olejnik et al. | 424/427 |
| 6,162,487 A | 12/2000 | Darouiche | |
| 6,206,916 B1 | 3/2001 | Furst | |

(Continued)

FOREIGN PATENT DOCUMENTS

EP 0544948 A1 6/1993
KR 2001-018344 A 3/2001

(Continued)

OTHER PUBLICATIONS

Pandey et al., Intracapsular ring sustained 5-fluorouracil delivery system for the prevention of posterior capsule opacification in rabbits: a histological study, J Cataract Refract Surg Jan. 2002 28 (1): 139-48.

(Continued)

*Primary Examiner* — Isis Ghali
(74) *Attorney, Agent, or Firm* — The Dobrusin Law Firm, P.C.

(57) ABSTRACT

A surgical device and method of making and using the same for implantation in a body of a mammal. One preferred device is prepared to include an elongated member. A region includes a pharmaceutical agent and a bioerodible material, a biodegradable material a bioavailable material or a mixture thereof.

20 Claims, 3 Drawing Sheets

U.S. PATENT DOCUMENTS

| | | | |
|---|---|---|---|
| 6,322,592 B2 | 11/2001 | Lucas et al. | |
| 6,352,542 B1 | 3/2002 | Snyder | |
| 6,692,759 B1 * | 2/2004 | Wong et al. | 424/423 |
| 7,163,543 B2 * | 1/2007 | Smedley et al. | 606/107 |
| 7,354,574 B2 * | 4/2008 | Peyman | 424/78.04 |
| 2001/0004708 A1 | 6/2001 | Nagai | |
| 2002/0099438 A1 | 7/2002 | Furst | |

FOREIGN PATENT DOCUMENTS

| | | |
|---|---|---|
| WO | WO 00/62760 | 10/2000 |
| WO | WO 01/32140 | 5/2001 |
| WO | WO 02/100318 | 12/2002 |
| WO | WO 03/061625 | 7/2003 |

OTHER PUBLICATIONS

Shi W et al., Prolongation of corneal allograft survival in mice with a cyclosporine drug delivery system implant, Chung Hua Yen Ko Tsa Chih Aug. 2002 38 (8): 502-5.

Mantripragada, S., A lipid based depot (DepoFoam technology) for sustained release drug delivery, Prog Lipid Res Sep. 2002 41 (5) 392-406.

Das et al., Effect of vancomycin on *Staphylococcus epidermidis* adherence to poly(methyl methacrylate) intraocular lenses, J Cataract Refract Surg Apr. 2002 28 (4): 703-8.

Cheng et al., Treatment or prevention of herpes simplex virus retinitis withintravitreally injectable crystalline 1-0-hexadecylpropanediol-3-phospho-ganciclovir, Invest Ophthalmol Vic Sci Feb. 2002; 43 (2): 515-21.

Herrero-Vanrell et al., Biodegradable microspheres for vitreoretinal drug delivery, Adv Drug Deliv Rev Oct. 31, 2001; 52 (1): 5-16.

Herrero-Vanrell et al., Biodegradable PLGA microspheres loaded with ganciclovir for intraocular administration. Encapsulation technique, in vitro release profiles, and sterilization process, Pharm Res Oct. 2000; 17 (10): 1323-8.

Jaffe et al., Fluocinolone acetonide sustained drug delivery device to treat severe uveitis, Ophthalmology Nov. 2000; 107 (11); 2024-33.

Jaffe et al., Safety and pharmacokinetics of an intraocular fluocinolone acetonide sustained delivery device, Invest Ophthalmol Vis Sci Oct. 2000; 41 (11); 3569-75.

Kunou et al., Long-term sustained release of ganciclovir from biodegradable scleral implant for the treatment of cytomegalovirus retinitis, J Control Release Aug. 10, 2000; 68(2): 263-71.

Einmahl et al., Concomitant and controlled release of dexamethasone and 5-fluorouracil from poly(ortho ester), Int J Pharm Aug. 20, 1999; 185(2): 189-98.

Tetz et al., Inhibition of posterior capsule opacification by an intraocular-lens-bound sustained drug delivery system: an experimental animal study and literature review, J Cataract Refract Surg Oct. 1996; 22 (8): 1070-9.

Rabowsky et al., The use of bioerodible polymers and daunorubicin in glaucoma filtration surgery, Ophthalmology May 1996; 103 (5): 800-7.

Nishi et al., Effect of intraocular sustained release of indomethacin on postoperative inflammation and posterior capsule opacification, J Cataract Refract Surg 1996; 22 Supp. 1: 806-10.

Chetoni et al., Ocular mini-tablets for controlled release of timolol: evaluation in rabbits, J Ocul Pharmacol Ther 1996 Fall; 12 (3): 245-52.

Kiremitci-Gumusderelioglu et al., A novel MMC-loaded pHEMA drainage device for the treatment of glaucoma: in vitro and in vivo studies, J Biomater Sci Polym Ed 1996; 7 (1): 857-69.

Borhani et al., Suppression of experiemental proliferative vitreoretinopathy by sustained intraocular delivery of 5-FU, Int Ophthalmol 1995; 19 (1): 43-9.

Joshi A., Microparticulates for ophthalmic drug delivery, J Ocul Pharmacol 1994 Spring; 10(1): 29-45.

Rahimy et al., Polysulfone capillary fiber for intraocular drug delivery: in vitro and in vivo evaluations, J Drug Target 1994; 2 (4): 289-98.

Chang DF et al., Two Clinical trials of an intraocular steriod delivery system for cataract surgery, Trans Am Ophthalmol Soc. 1999; 97: 261-74; discussion 274-9.

DuBosar, Ryan, Intraocular steriod delivery system completes FDA phase 2 trial; New drug delivery system could make postop cataract managment easier and more efficient, Ocular Surgery News, a SLACK Incorporated newspaper, Nov. 1, 1997.

Chang, David F., An Intraocular Steriod Delivery System for Cataract Surgery, British Journal of Ophthalmology, Mar. 9, 2001.

* cited by examiner

SUSTAINED RELEASE IMPLANTABLE EYE DEVICE

CLAIM OF BENEFIT OF FILING DATE

This application claims the benefit of the filing date of U.S. Provisional application No. 60/462,284 (filed Apr. 11, 2003), hereby expressly incorporated by reference.

TECHNICAL FIELD

The present invention relates to biomedical implants and more particularly to implants that incorporate a sustained release pharmaceutical agent, such as a steroid, an antibiotic, an anti-inflammatory agent or a combination thereof.

BACKGROUND

The present invention relates to the subject matter of co-pending U.S. Ser. No. 10/346,671, filed Jan. 17, 2003 and PCT US03/01388 filed Jan. 17, 2003, the contents of which are hereby incorporated by reference for all purposes. There is a need in the health care industry to package pharmaceuticals in alternative ways to efficiently provide drug delivery, such as in a sustained release format, and particularly as applied to a biomedical device that is implanted in a body of an animal or human.

An object of the present invention is to provide an efficient technique and device for introducing a pharmaceutical agent into a body, particularly for sustained release following a surgical procedure.

Another object is to apply one or a plurality of sustained release pharmaceutical agents to a generally conventional implant design in a manner such that over time the active ingredient of the pharmaceutical agent becomes bioavailable within the body.

The following items may be relevant to the present invention and are hereby incorporated by reference herein for all purposes; for instance it is contemplated that the methods, therapies or devices of the disclosed subject matter may be adapted to employ the novel features of the present invention: U.S. Pat. Nos. 4,853,224; 5,876,438; 5,843,184; 5,616,122; 5,375,611; 5,273,751; and 5,401,880.

SUMMARY OF THE INVENTION

The present invention is predicated upon the discovery of an improved method for providing a sustained release of a dose of a pharmaceutical agent, comprising the steps of:

providing an elongated member selected from a suture, a staple, dental implant, clip or a lumen; and applying to the implant a sustained release medium and a pharmaceutical agent selected from an antimicrobial, an anti-thrombotic, an antiseptic, an antifungal, a chelating, an anti-coagulant, antibiotic, an anti-inflammatory, a steroid, an anti-glaucomatous or a combination thereof.

The invention also contemplates embodiments wherein the sustained release medium and the pharmaceutical layer are applied for defining a multi-layered structure, a structure having the pharmaceutical agent dispersed in the sustained release medium or a combination thereof;

wherein the sustained release medium is applied to optionally define a barrier layer over at least one region of a pharmaceutical agent;

wherein the sustained release medium comprises a material provided in a state selected from solid, semi-solid, liquid, gel, amorphous solid, crystalline solid, freeze dried, spray-dried, or supercooled;

wherein over a major portion of its length, the outer surface of the member has the sustained release medium and the pharmaceutical agent applied thereto, and is selected from a smooth surface an irregular surface, a stepped surface, a tapered surface, a surface having no slope or a combination thereof;

wherein at least one of the sustained release medium, the pharmaceutical agent, or a combination of both, is applied to the implant by a step including, spraying, dipping, swabbing, brushing, rolling, curtain coating, doctor blading, vapor deposition or combinations thereof;

wherein the pharmaceutical agent is applied to the member along the length of the implant as a continuous layer or an intermittent layer;

wherein the pharmaceutical agent is optionally applied to the member by producing a mixture that includes at least one porogenic agent, compacting or shaping the mixture to its desired form, treating the product obtained in such a way that the porogen is removed, and introducing pharmaceutical agent where the porogen used to be; and wherein the pharmaceutical agent is applied to the member at a surgical site or at a site remote from the surgical site.

The present invention also contemplates a device provided according to the above method, and a therapy employing a device prepared according to the above method.

BRIEF DESCRIPTION OF THE DRAWINGS

Like parts are denoted by like reference numerals in the different embodiments.

DETAILED DESCRIPTION

Figure 1:
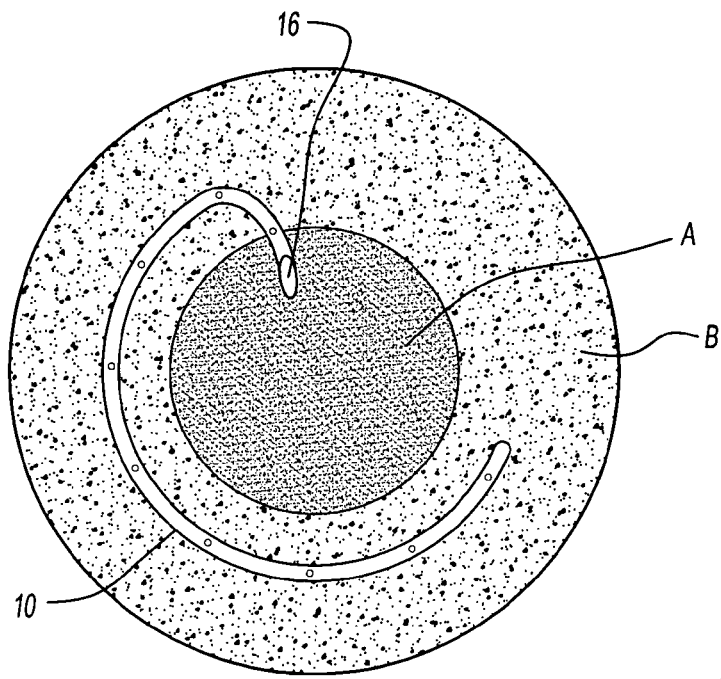
FIG. 1 is a top view of an eye having a cornea A, showing an implant device herein inserted through into a sub-conjunctival space B.

The present invention is directed generally to a method (and articles therefrom) for providing a medicated implant member 10, comprising the steps of:

providing an elongated, deformable, member 10 that is solid, hollow, porous, or a combination thereof; and covering the member with a layer 12, such as one including a sustained release medium, optionally with a pharmaceutical agent, such as an agent selected from the group consisting of an anti-inflammatory, a steroid, an antibiotic or a combination thereof, wherein the sustained release medium is provided as a barrier layer that has an outer surface 14, which is (i) tapered, stepped, free of slope or a combination thereof, and which is (ii) disposed over a pharmaceutical agent layer, a mixture with a pharmaceutical agent dispersed throughout, or a combination thereof; wherein the member is configured to have an outer surface that is selected from a smooth surface, an irregular surface defined for providing a cavity for receiving the pharmaceutical agent, or a combination thereof; and further wherein the sustained release medium is a material selected from a biodegradable material, a bioerodable material, a bioavailable material or a combination thereof.

Preferably, the pharmaceutical agent is selected from an antimicrobial, an antithrombotic, an antiseptic, an antifungal, a chelating, an anticoagulant, antibiotic, an anti-inflammatory, a steroid, an antiglaucomatous or a combination thereof.

Particularly preferred embodiments of the present invention contemplate that the elongated member is formed to define an article selected from a suture, a staple, a dental implant, a clip or a lumen.

With respect first to sutures according to the present invention, the sutures for which the present invention is applicable include any art-disclosed sutures (for use anywhere on or within a body), and thus may include sutures that have a needle integrated therewith, a chamfered or otherwise sharpened end (e.g. such as the optional ends 16 of the implants of FIGS. 2 and 3) or sutures to which a needle is attached. The sutures may include a crimpable portion that plastically deforms upon application of a pressure. The sutures may be suitable for knotted attachment or knotless attachment. For example, the sutures of the present invention may also be provided to include or be adapted to be in cooperative association with a suitable art-disclosed suture anchor or suture lock, which itself may include a portion that is a material selected from biodegradable material, a bioerodable material, a bioavailable material or a combination thereof.

The suture may be provided as a continuous length (requiring cutting), such as on a reel, or pre-cut in predetermined lengths. In one embodiment, it is possible that the suture is coated at the point of surgery with a pharmaceutical agent and biodegradable material, a bioerodable material, a bioavailable material or a combination thereof. For example, the suture is passed through a dispenser for pharmaceutical agent, which allows a surgeon or other person at a surgical site to apply the agent at time of surgery. The dispenser may also be adapted for dispensing biodegradable material, a bioerodable material, a bioavailable material or a combination thereof. The dispensing of pharmaceutical agent and biodegradable material, bioerodable material, bioavailable material or a combination thereof, preferably is performed through consecutive steps, or simultaneously. It is also possible that the biodegradable material, a bioerodable material, a bioavailable material or a combination thereof is a curable material, (e.g., a moisture, heat or radiation cure), and thus may be subjected to curing during the application process.

The present invention also contemplates the use of a suture coated according to the teachings herein, and preferably coating the suture so that the risk of unfavorably altering the systemic flora of a patient with possible opportunistic infections in secondary, unrelated sites and the risk of selecting out for resistant bacterial in the patients normal flora are both substantially reduced as compared with the use of intravenously administered antibiotics. It is thus believed that use of the sutures or other implants of the present invention, when coated to include a pharmaceutical agent, will substantially reduce the likelihood of wound infection at the primary site of occurrence without the risks of systemic side effects.

In another embodiment, the above teachings can be applied to the coating of staples or clips used to close wounds.

It should also be appreciated that the present invention need not necessarily employ a pharmaceutical agent, but may instead involve coating a member with a sustained release medium in a manner to function as a mask or the like for the member. For example, the sustained release medium may be employed as a mask for ostia.

The present invention applies not only to treatment of skin wounds, but also applies as well to other wound sites potentially susceptible to infection, and which currently are typically closed with staples or sutures. Thus, the present invention is applicable to the formation of staples or sutures for use in intestinal closures (e.g., with a simultaneous or serial staple machine), as well as wound sites resulting from laproscopic surgery of the abdomen, thorax, pelvis, mediastinum, sinuses, retroperitoneum or other body cavity or site where endoscopic or open surgical techniques are employed. Dental surgery may also employ the methods and devices of the present invention. For example, a dental implant (including portions thereof for positioning at or above (or possibly even below) the gum-line, such as an anchor or support post of a dental implant for seating in a jawbone, a dental prosthesis, an implant collar or a combination) thereof may be coated according to the methods of the present invention.

For cosmetic plastic surgery or other surgical procedures, the invention also envisions the use of one or more wound modulators or one of the pharmaceutical agents to reduce or eliminate scarring or uneven healing of a surface skin, subcutaneous or deeper wound. This would apply equally to ophthalmic plastic surgical procedures.

In another highly preferred embodiment, the invention could apply bioabsorbable, bioerodable or other sustained release antiinfective agent to a length of flexible material comprising a stent or catheter. For example stents used to keep the lacrimal passage open during healing after surgery on the lacrimal caniliculi, punctae or lacrimal sac of the eye and an ocular surface. Wound modulators could reduce internal scarring or phimosis which could impede the success of this sort of drainage system procedure. Similarly, such wound modulators could be applied to other stents or catheters used for urogenital procedures including anastomoses or transurethral prostate resection surgeries, biliary tract surgeries or other surgeries where temporary or continued flow through a lumen is desired.

One skilled in the art of neurosurgery would recognize that flow through a ventriculoperitoneal or vetriculoatrial shunt could become impeded by scar tissue formation or aggregation of clot, fibrin, or the like at the proximal or distal openings of the tube. The occlusion of the lumen or ostia of such a shunt could result in an undesirable increase in the intracranial pressure for which the shunt was placed. Wound modulators or other pharmaceuticals such as tissue plasminogen activators, other anticoagulants, or the like could be applied to one or both ends of such a shunt device in varying combinations so as to limit the risk of early or late occlusion of such a shunt.

The shunts used for ophthalmic surgery may also become occluded by excess fibrosis or scar tissue formation and wound modulators and/or anti-scarring agents could be applied to the surface of such shunts to reduce this undesired response and maintain the constant flow of fluid through the lumen of the shunt and into the subconjunctival space unimpeded.

A shunt device for glaucoma may exhibit a wide variety of configurations, some of which have adjacent tubes, plates, valves or other appendages. In order to create a graded flow through the shunt device which increases over time to coincide with healing and/or increased resitance to flow from the system as a result of healing, the shunt may be employed with a material selected from a biodegradable material, a bioerodable material, a bioavailable material or a combination thereof to reduce flow on a graded and/or temporary basis.

In one iteration, the agent could partially fill all or part of the length of a lumen of a glaucoma drainage tube or other hollow implant member so as to reduce the effective opening of the tube. Since pressure is dependant upon resistance within the system, the narrower the effective lumen, the higher the pressure, while the larger the lumen the lower the pressure. As the biodegradable material, a bioerodable material, a bioavailable material or a combination thereof re-absorbs, dissolves, or otherwise dissipates, the degree of opening of a lumen (with an interior passageway coated) of the tube could be increased over time, affording less resistance and increased flow. A variety of geometric crossections of a lumen could be configured so as to regulate the change in flow over time in a linear, nonlinear, or logarithmically increasing fashion.

Figure 2:
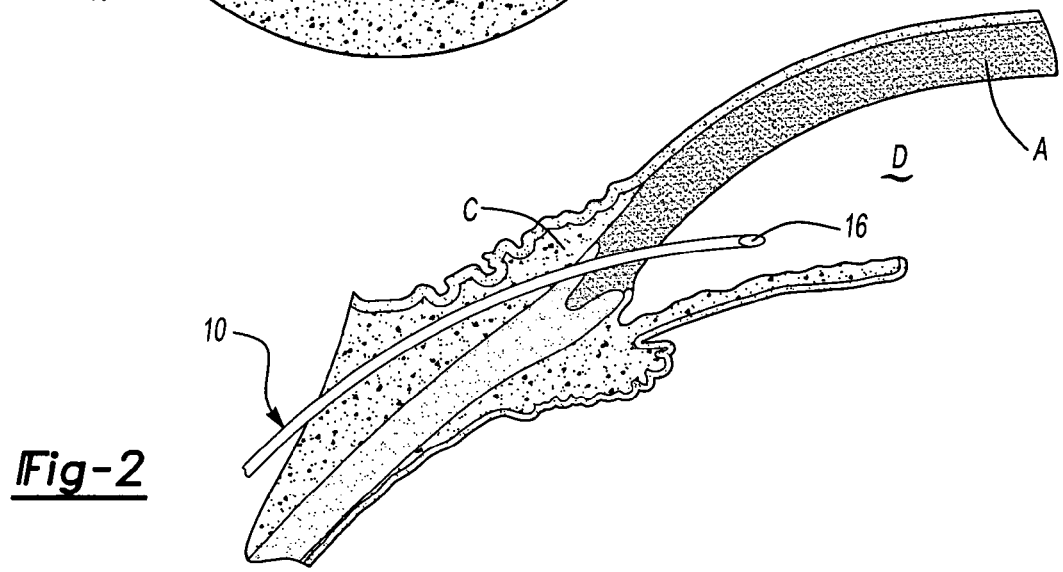
FIG. 2 is a side sectional view of an eye showing an implant device (e.g. a tube) herein disposed through a conjuctiva C in an anterior chamber D of an eye.
Figure 3:
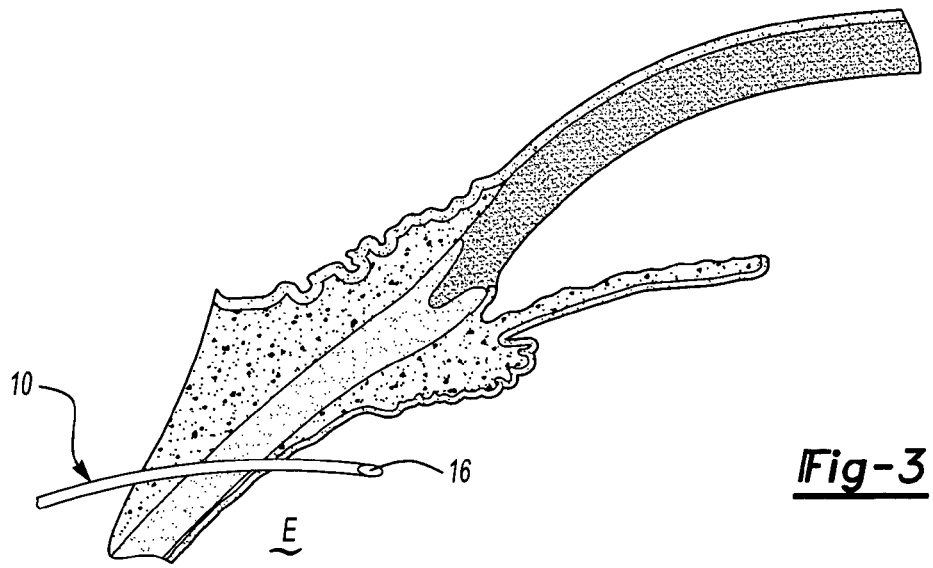
FIG. 3 is a side sectional view of an eye showing an implant device (e.g. a tube) in the pars plana E portion of a vitrectomized eye.

FIGS. 1-3 illustrate examples of how an implantable member 10 of the present invention might be employed in an eye for ophthalmological surgical procedures. An implantable member of the present invention (preferably having been fabricated to include a pharmaceutical agent as described herein) such as a tube, shunt or otherwise is inserted into an eye, such that a leading end of the member is located in the anterior chamber of the eye, in the pars plana portion of the eye or both.

Figure 4:
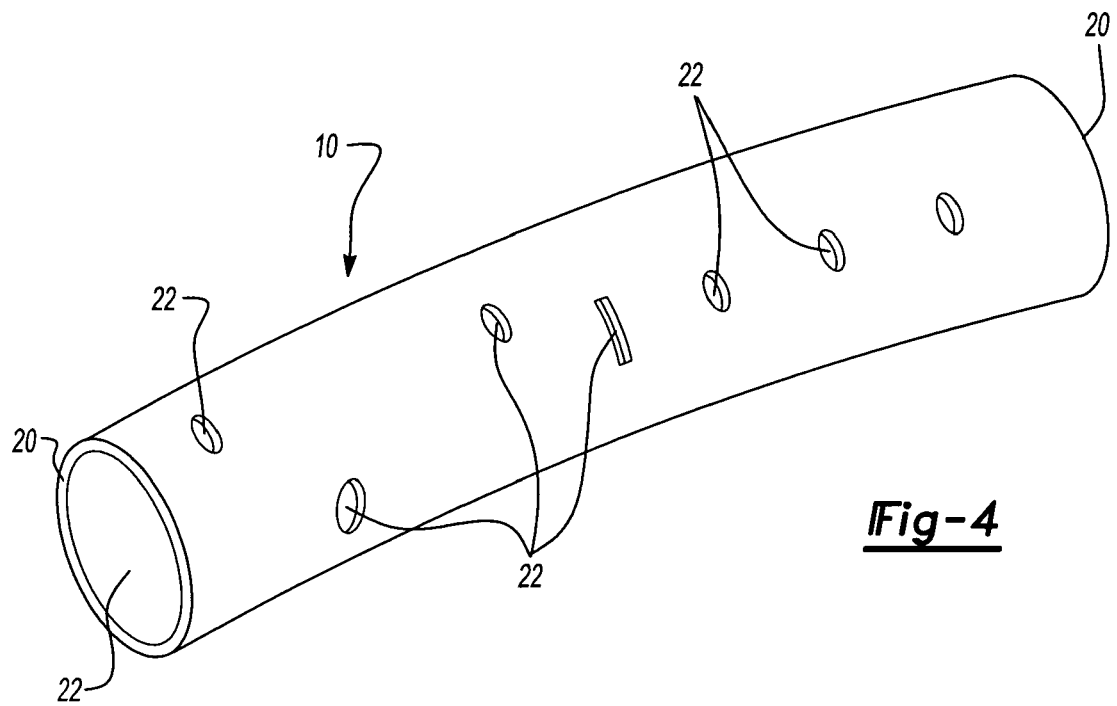
FIG. 4 is a perspective view of an implantable member of the present invention to illustrate various different possible openings that can be employed in the member to achieve a sustained release in accordance with the present invention.
Figure 5:
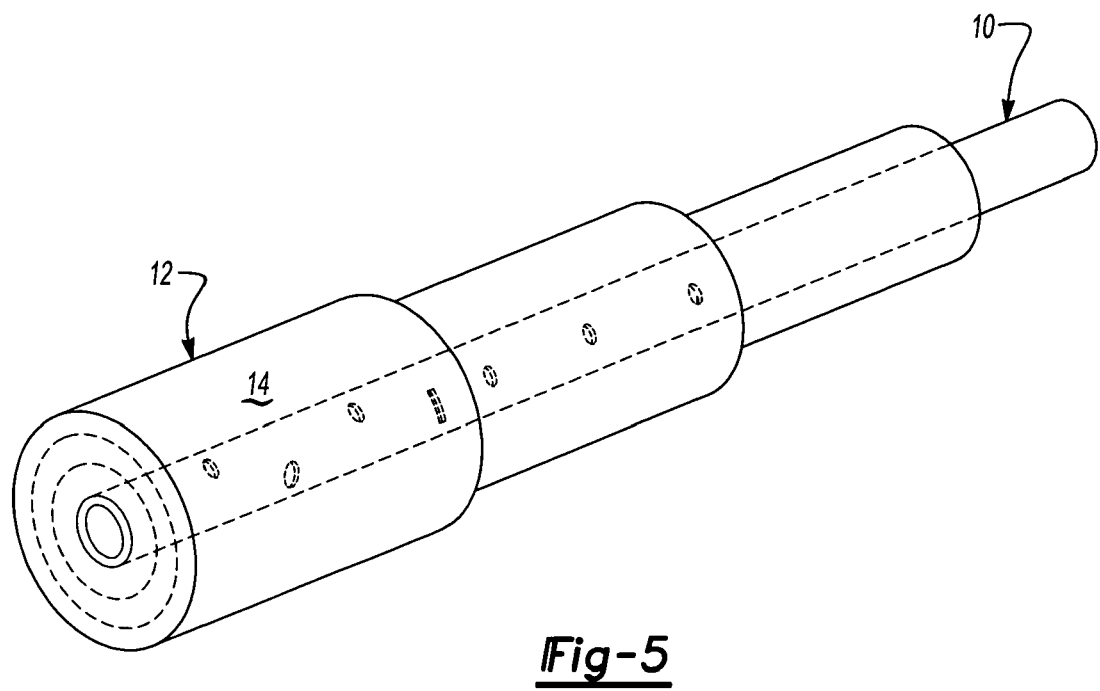
FIG. 5 is a perspective view of another alternative embodiment including an implantable member.
Figure 6:
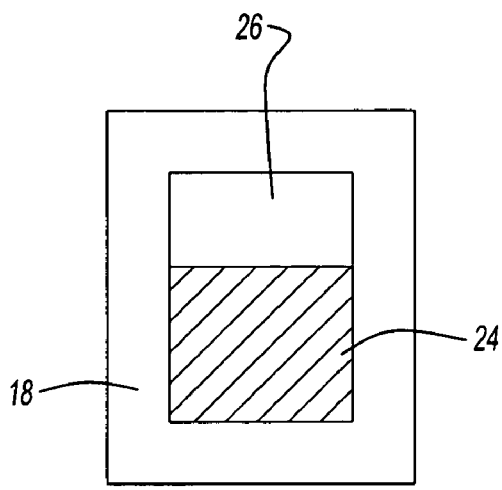
FIGS. 6-9 are sectional view of devices to illustrate different approaches to loading the devices with a pharmaceutical agent, sustained release medium or both.
Figure 7:
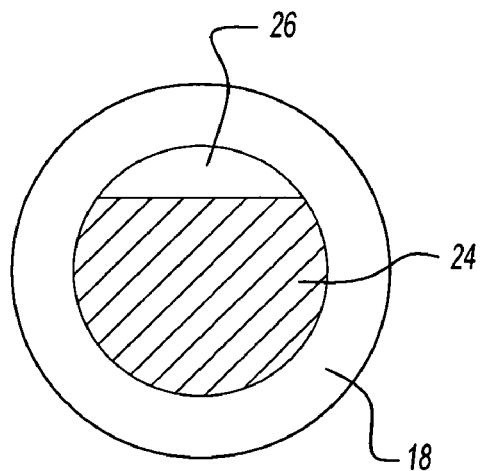
Figure 8:
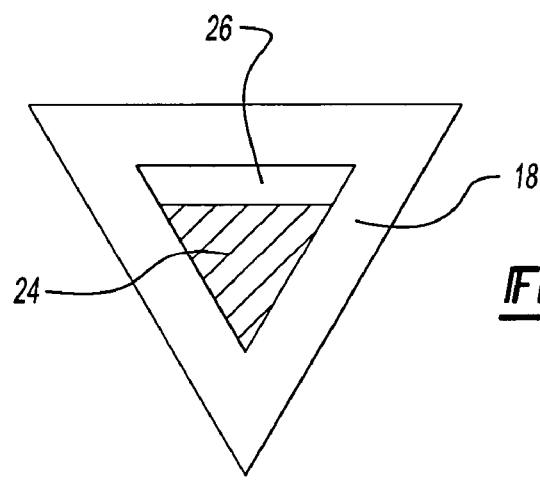
Figure 9:
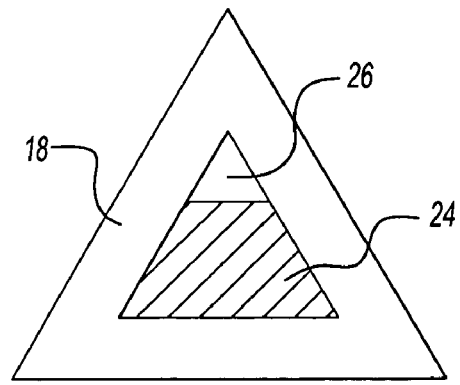

In another aspect, the biodegradable material, bioerodable material, bioavailable material or a combination thereof could coat an outer portion of the shunt to cover some of a number of different ostia, pores or other openings 22 between the lumen of the device and the area outside the wall of the device. The coating could be of variable thicknesses in different areas overlying different numbers of ostia, pores, slits or the like so as to allow for continued increase in the exposed ostia over time in a linear, nonlinear or logarithmic fashion so as to result in a desired resistance within the tubing or shunt device to achieve a predetermined intra-ocular pressure. With reference to FIGS. 4 and 5, it is seen how the implantable member may be adapted to have a plurality of openings of the same or different size or shape, and may have an optional end opening 22'. One specific approach is to have a substantially solid walled member (e.g., a plastic tube, a metal tube or otherwise, and particularly having a fixed inner and outer dimension such as the diameter) having a plurality of openings (e.g., of fixed size and shape) formed along the length of the opening. The member can be loaded with pharmaceutical agent, sustained release medium or a combination thereof. The openings are adapted so that as the layer 14 diminishes, the openings of the implantable member become exposed and thereby provides gradually increasing volumes or areas through which the pharmaceutical agent, sustained release medium or combination thereof may escape from within the member. By selectively controlling the size, shape and location of the openings, and the nature of the layer 14, the timing of when the pharmaceutical agent, sustained release medium or a combination thereof is released through an opening can be controlled.

In one very highly preferred embodiment, the entire glaucoma shunt device may consist of a length of tube or geometric length of material with a lumen with biodegradable material, bioerodable material, bioavailable material or a combination thereof, placed either on the surface or within the lumen of the shunt, as described above, in which the tube is like a length of suture applied to a needle. The needle could be used to place the tube or shunt through the iridocorneal angle region from either an ab interno or ab externo fashion, then the tube could be woven through the subconjunctival space, much like a length of suture, though one or more quadrants until the desired length of tube has been fully placed. The needle could then be disengaged from the device, perhaps by snapping off, snipping with a scissors, or the like.

The invention anticipates that once a highly desired intraocular pressure is reached, a mechanism for halting the erosion of the agent, perhaps by exposure to a particular frequency of light or other mechanism of altering polymerization or erodable characteristics could be applied to fixate the state of the device/agent combination at a given point in time. A reversal of such a fixation is similarly anticipated.

In another highly preferred embodiment, limitation of excess flow from a tube or shunt could be controlled by applying a photoactive polymer around the extent of the tube at one or more locations along its length, much like a constricting sphincter. Polymers currently exist where the properties of the polymer, particularly size, shape, and flexibility can be altered by exposure to varying wavelengths of visible or invisible light. In the case of excess flow, a focal surrounding element could be altered to shrink and thus constrict the lumen of a flexible-walled shunt in one or more areas to reduce or eradicate the lumen and thus increase resistance either from reduction of the lumen flow itself or from prohibiting access of the fluid from the lumen to other pores, slits, holes, ostia or the like further downstream. The invention further contemplates that such circumferentially applied adjustable polymers could be altered to expand and thus widen the lumen in cases where the flow is undesirably lowered. In such a case, we anticipate that such polymer could exist along either part of or the entire length of the device This application for variable flow over time through a lumen is described above for application in glaucoma shunt device surgery, but can also be anticipated to apply to neurosurgical shunts or the like in any medical instance where flow through a tube or other viscus is required or desired.

The shape of a particular device of the present invention may vary as desired, whether from device to device or along the length of a single device. As seen in FIGS. 6-9, they may be round, polygonal (e.g., triangular, rectangular, pentagonal, hexagonal, octagonal or otherwise). The employment of optional openings such as openings 22 or 22' in FIG. 4 will allow the pharmaceutical agent with sustained release medium 24 to escape from within the implantable member (e.g. from within a lumen). Of course it is also possible to maintain open ends such as opening 22 in FIG. 4, for escape. It should be appreciated that the openings may be formed during the step of forming the implant member itself, it may be formed during a subsequent processing step or both. For example, an implant member might be formed by extruding through a first tool, followed by applying a second tool to form the openings. In another example, an implant member might be molded in a mold that is adapted for forming the openings upon molding. Other approaches are also possible.

FIGS. 6-9 also illustrate possible approaches to control of matter flow through a hollow elongated member including a lumen, whether of a type of with openings (one such example being illustrated in FIGS. 4-5), or without openings. As can be appreciated a wall 18 defining the lumen can be of a suitable shape, such as a rectangular, circular, or triangular section. The member is filled with sustained release medium 24 leaving a head space 26 through which matter such as a fluid or stream of particles may pass. The size of the headspace will increase over time. Depending upon how the member is loaded with the sustained release medium, the rate of headspace increase can be selectively controlled. For example, the sustained release medium may be employed to increase a rate of flow through the lumen linearly over time, to increase a rate of flow through the lumen over time followed by a period of slower increase of flow rate, so that the rate of increase of flow gradually decreases, or so that the rate of increase of flow gradually increases.

A practitioner skilled in the art will also recognize the potential benefits of adding other or additional pharmaceutical agents, depending on the nature of the application, and future as yet unknown applications of pharmaceutical agents which, may include other anti-infective, anti-ocular hypertensive anti-inflammatory, anti-angiogenesis, anti-proliferative, anti-neoplastic, growth factors, stimulatory agents or, even vectors for introduction of gene therapy or gene modulating agents.

The particular bio-compatible material for use as a sustained release medium may be selected as desired. Such material may be provided for securing onto an ophthalmologic implant in a form selected from a liquid, a powder, a gel, or a mixture thereof. Solid materials may be crystalline, amorphous, or a mixture thereof, either in their as provided state or in an intermediate or final state. The material may include or consist essentially of a small molecule, an oligomer, a polymer (organic, biological or a combination thereof), or combinations thereof. Preferably the material is of one or more pH levels that are compatible with the patient.

The specific material may vary. Examples of materials that may be employed for providing a sustained release include, without limitation, caprolactones (e.g., a polyactide-coglycolide-co-caprolactone (PGLC) polymer), multivesicular liposomes (e.g., with unilamellar vesicles, mutilamellar vesicles, neosomes, closely packed non-concentric vesicles (such as DEPOFOAM™), or combinations thereof), salts (e.g., an ammonium salt of 1-0-hexadecylpropanediol-3-phospho-ganiclovir (HDP-P-GCV)), poly(lactic acid), poly (glycolic acid), copolymers of lactic and glycolic acids, poly (DL-lactide-co-glycolide) (PLGA) or blends of PLGA of different molecular weights, poly (orthoester), acrylic polymers, methacrylic polymers, poly (hydroxyethylmethacrylate), polysulfone or mixtures thereof. Cellulose materials, starch materials, other carbohydrate materials or the like may be employed as well. The present invention contemplates that the material employed may be one that is not listed herein and the omission from the above list should not be construed as limiting of the scope of the invention.

Additional examples of other materials for sustained release and/or pharmaceutical agents may be gleaned from a review of WO 02/100318 and WO 01/32140, which are hereby expressly incorporated by reference.

In yet another embodiment, it is contemplated that the devices made according to the present invention may, in addition to or in lieu of any pharmaceutical agent, may include fluorescent markers or other markers that are capable of detection by suitable detection techniques, such as radiological techniques. Accordingly, wound progress may be monitored after completion of surgery. Without limitation, a further specific application might include markers that have an associated monoclonal antibody, which interact with surface antigens associated with cells.

The markers can be employed in suitable doses so that periodically they are predictably released and detected. In this manner, the local concentration of markers that are detected near the site of interest can be correlated with the reduction of the size of the wound site or other mass under consideration.

Additional embodiments of the present invention may be gleaned from a review of the attached drawings of FIGS. 1-9. For example a sustained release medium may be omitted in favor of the use only of a pharmaceutical agent or a pharmaceutical agent in another medium. Mixtures of sustained release medium and pharmaceutical agent may be homogeneous or it may vary throughout a volume of material. Of course, also as discussed a layered approach such as in FIG. 5 and in US 03/01388, Ser. No. 10/346,671, incorporated by reference may be used. The layers of sustained release medium may be internal of an implant member or external of the implant member.

While a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

What is claimed is:

1. An implantable device, comprising:
   a) an implantable elongated hollow glaucoma drainage tube including a solid walled plastic lumen having a lumen section that extends into an eye and wraps generally circularly around cornea of said eye and includes a flow passage so that when the tube is implanted within the eye the tube has a first end located in a first portion of the eye and a second end located in a second portion of the eye and the flow passage spans between the first end and the second end; and
   b) a sustained release medium including caprolactone and an antimicrobial within an interior of the lumen that is filled with the sustained release medium to define a head space passage that increases its degree of opening over time as matter is passed through the lumen;
   wherein the lumen has a circular cross section fixed inner and outer dimension, defining a lumen diameter, the tube includes a plurality of openings of a fixed size and shape, through which the sustained release medium escapes, and the sustained release medium comprises a solid material.

2. The device of claim 1, wherein the lumen has open ends.

3. The device of claim 1, further comprising a radiological detectable marker that are monitored to correlate with a reduction in size of a wound site or a mass under consideration.

4. The device of claim 1, where the sustained release material is provided as layers.

5. The device of claim 2, further comprising a coating of the sustained release material on an exterior of the lumen and covering the openings, so that as a layer diminishes, the openings of the lumen become exposed and thereby provides gradually increasing volumes or areas through which the sustained release material that is filled within the lumen escapes from the lumen.

6. The device of claim 1, wherein the first end when implanted is located in an anterior chamber of the eye or in a pars plana portion of the eye.

7. The device of claim 6, wherein the lumen has open ends.

8. The device of claim 6, further comprising a radiological detectable marker that are monitored to correlate with a reduction in size of a wound site or a mass under consideration.

9. The device of claim 7, further comprising a radiological detectable marker that are monitored to correlate with a reduction in size of a wound site or a mass under consideration.

10. The device of claim 6, where the sustained release material is provided as layers.

11. The device of claim 7, where the sustained release material is provided as layers.

12. The device of claim 8, where the sustained release material is provided as layers.

13. The device of claim 6, further comprising a coating of the sustained release material on an exterior of the lumen and covering the openings, so that as a layer diminishes, the openings of the lumen become exposed and thereby provides gradually increasing volumes or areas through which the sustained release material that is filled within the lumen escapes from the lumen.

14. The device of claim 7, further comprising a coating of the sustained release material on an exterior of the lumen and covering the openings, so that as a layer diminishes, the openings of the lumen become exposed and thereby provides gradually increasing volumes or areas through which the sustained release material that is filled within the lumen escapes from the lumen.

15. The device of claim 9, further comprising a coating of the sustained release material on an exterior of the lumen and covering the openings, so that as a layer diminishes, the openings of the lumen become exposed and thereby provides gradually increasing volumes or areas through which the sustained release material that is filled within the lumen escapes from the lumen.

16. The device of claim 12, further comprising a coating of the sustained release material on an exterior of the lumen and covering the openings, so that as a layer diminishes, the openings of the lumen become exposed and thereby provides gradually increasing volumes or areas through which the sustained release material that is filled within the lumen escapes from the lumen.

17. The device of claim 4, wherein erosion of the layers is halted when a desired intraocular pressure is reached.

18. The device of claim 16, wherein erosion of the layers is halted when a desired intraocular pressure is reached.

19. The device of claim 1, wherein the device includes a focal surrounding element that can be altered to shrink and constrict the lumen.

20. The device of claim 16, wherein the device includes a focal surrounding element that can be altered to shrink and constrict the lumen.

* * * * *